US006939308B2

(12) United States Patent
Chassaing et al.

(10) Patent No.: US 6,939,308 B2
(45) Date of Patent: Sep. 6, 2005

(54) ACOUSTIC SENSOR ARRAY FOR NON-INVASIVE DETECTION OF CORONARY ARTERY DISEASE

(75) Inventors: Charles E. Chassaing, Raleigh, NC (US); Hung Nguyen, Cary, NC (US)

(73) Assignee: MedAcoustics, Inc., Raleigh, NC (US)

( * ) Notice: Subject to any disclaimer, the term of this patent is extended or adjusted under 35 U.S.C. 154(b) by 484 days.

(21) Appl. No.: 10/291,129

(22) Filed: Nov. 8, 2002

(65) Prior Publication Data

US 2003/0069506 A1 Apr. 10, 2003

Related U.S. Application Data

(62) Division of application No. 09/188,434, filed on Nov. 9, 1998, now Pat. No. 6,193,668, which is a division of application No. 09/734,448, filed on Dec. 11, 2000, now Pat. No. 6,478,746.

(51) Int. Cl.$^7$ ............................................. A61B 5/00
(52) U.S. Cl. ...................... 600/504; 128/897; 600/454
(58) Field of Search ................................ 600/504–507, 600/554; 128/897

(56) References Cited

U.S. PATENT DOCUMENTS

| | | | |
|---|---|---|---|
| 3,442,264 A | 5/1969 | Levitt ........................ 128/2.06 |
| 3,573,394 A | 4/1971 | Birnbaum ................... 128/2.05 |
| 3,799,147 A | 3/1974 | Adolph et al. ............. 128/2.05 |
| 3,903,733 A | 9/1975 | Murayama et al. .......... 73/71.4 |
| 4,008,408 A | 2/1977 | Kodama ..................... 310/9.1 |
| 4,054,808 A | 10/1977 | Tanaka ....................... 310/323 |
| 4,094,308 A | 6/1978 | Cormier ................ 128/2.05 R |
| 4,146,955 A | 4/1979 | Young, Jr. et al. ............. 29/594 |
| 4,183,249 A | 1/1980 | Anderson .................... 73/626 |
| 4,226,248 A | 10/1980 | Manoli ........................ 128/773 |
| 4,234,813 A | 11/1980 | Iguchi et al. ................ 310/366 |
| 4,255,791 A | 3/1981 | Martin ........................ 364/514 |

(Continued)

FOREIGN PATENT DOCUMENTS

| | | |
|---|---|---|
| DE | 32 34 584 A1 | 3/1984 |
| DE | 3531399 A1 | 3/1986 |
| EP | 0194823 A2 | 9/1986 |
| EP | A 0 201 421 | 11/1986 |
| EP | 0325805 A2 | 8/1989 |
| EP | A 0 528 279 | 2/1993 |
| FR | A 2 507 424 | 12/1982 |
| GB | 2166871 A | 5/1986 |
| GB | 2188732 A | 10/1987 |
| WO | WO/90-08506 | 8/1990 |
| WO | WO 93/22970 | 11/1993 |
| WO | WO A 94 05207 | 3/1994 |
| WO | WO 95/06525 | 3/1995 |

OTHER PUBLICATIONS

"Gabor Spectrogram," DSP Software Development, National Instruments, Austin, TX.

Akay et al., "Application of Adaptive FTF/FAEST Zero Tracking Filters to Noninvasive Characterization of the Sound Pattern Caused by Coronary Artery Stenosis Before and After Angioplasty," Annals of Biomedical Engineering, vol. 21, pp. 9–17 (1993).

(Continued)

*Primary Examiner*—Robert L. Nasser
(74) *Attorney, Agent, or Firm*—Myers Bigel Sibley & Sajovec PA

(57) ABSTRACT

Methodology for determining the bounds of a patient's acoustic window is described. Medical application acoustic array designs with apertures accommodated by patient acoustic windows and merged acoustic windows are exemplified.

20 Claims, 12 Drawing Sheets

U.S. PATENT DOCUMENTS

| | | | |
|---|---|---|---|
| 4,268,912 A | 5/1981 | Congdon | 367/163 |
| 4,308,870 A | 1/1982 | Arkans | 128/640 |
| 4,376,302 A | 3/1983 | Miller | 367/157 |
| 4,385,255 A | 5/1983 | Yamaguchi et al. | 310/335 |
| 4,387,378 A | 6/1983 | Henderson | 343/854 |
| 4,406,967 A | 9/1983 | Obara et al. | 310/366 |
| 4,413,630 A | 11/1983 | Anderson et al. | 128/661 |
| 4,424,465 A | 1/1984 | Ohigashi et al. | 310/335 |
| 4,428,380 A | 1/1984 | Wong et al. | 128/715 |
| 4,458,693 A | 7/1984 | Badzinski et al. | 128/715 |
| 4,491,051 A | 1/1985 | Barcus | 84/1.16 |
| 4,509,527 A | 4/1985 | Fraden | 128/671 |
| 4,546,777 A | 10/1985 | Groch et al. | 128/715 |
| 4,549,551 A | 10/1985 | Dyck et al. | 128/689 |
| 4,586,514 A | 5/1986 | Schlager et al. | 128/773 |
| RE32,180 E | 6/1986 | Chase | |
| 4,628,321 A | 12/1986 | Martin | 342/379 |
| 4,630,203 A | 12/1986 | Szirtes | 364/414 |
| 4,656,385 A | 4/1987 | Tanaka | 310/348 |
| 4,697,597 A | 10/1987 | Sanz et al. | 128/699 |
| 4,700,712 A | 10/1987 | Schmid | 128/699 |
| 4,712,565 A | 12/1987 | Katz et al. | 128/715 |
| 4,742,458 A | 5/1988 | Nathans et al. | 364/417 |
| 4,777,961 A | 10/1988 | Saltzman | 128/715 |
| 4,781,200 A | 11/1988 | Baker | 128/670 |
| 4,784,154 A | 11/1988 | Shirley et al. | 128/715 |
| 4,792,145 A | 12/1988 | Eisenberg et al. | 128/715 |
| 4,803,986 A | 2/1989 | Dufresne et al. | 128/385 |
| 4,803,996 A | 2/1989 | Peel et al. | 128/710 |
| 4,805,633 A | 2/1989 | Kotani et al. | 128/715 |
| 4,812,976 A | 3/1989 | Lundy | 364/413.06 |
| 4,821,584 A | 4/1989 | Lembke | 73/862.68 |
| 4,840,183 A | 6/1989 | Takahashi et al. | 128/715 |
| 4,842,411 A | 6/1989 | Wood | 356/376 |
| 4,862,144 A | 8/1989 | Tao | 340/573 |
| 4,862,361 A | 8/1989 | Gordon et al. | 364/413.06 |
| 4,862,897 A | 9/1989 | Eisenberg et al. | 128/715 |
| 4,905,706 A | 3/1990 | Duff et al. | 128/701 |
| 4,924,875 A | 5/1990 | Chamoun | 128/696 |
| 4,928,705 A | 5/1990 | Sekhar et al. | 128/773 |
| 4,947,859 A | 8/1990 | Brewer et al. | 128/715 |
| 4,957,369 A | 9/1990 | Antonsson | 356/376 |
| 4,967,760 A | 11/1990 | Bennett, Jr. et al. | 128/715 |
| 4,991,581 A | 2/1991 | Andries | 128/715 |
| 5,002,058 A | 3/1991 | Martinelli | 128/662 |
| 5,002,060 A | 3/1991 | Nedivi | 128/671 |
| 5,003,605 A | 3/1991 | Phillipps et al. | 381/67 |
| 5,010,889 A | 4/1991 | Bredesen et al. | 128/715 |
| 5,012,815 A | 5/1991 | Bennett, Jr. et al. | 128/715 |
| 5,025,809 A | 6/1991 | Johnson et al. | 128/715 |
| 5,035,247 A | 7/1991 | Heimann | 128/715 |
| 5,036,857 A | 8/1991 | Semmlow et al. | 128/715 |
| 5,056,201 A | 10/1991 | Kasuga et al. | 29/25.35 |
| 5,086,776 A | 2/1992 | Fowler, Jr. et al. | 128/661.09 |
| 5,109,863 A | 5/1992 | Semmlow et al. | 128/715 |
| 5,129,403 A | 7/1992 | Henriquez et al. | 128/773 |
| 5,140,992 A | 8/1992 | Zuckerwar et al. | 128/715 |
| 5,164,627 A | 11/1992 | Popek | 310/313 B |
| 5,176,153 A | 1/1993 | Eberhardt | 128/897 |
| 5,213,108 A | 5/1993 | Bredesen et al. | 128/715 |
| 5,218,969 A | 6/1993 | Bredesen et al. | 128/710 |
| 5,301,679 A | 4/1994 | Taylor | 128/773 |
| 5,315,512 A | 5/1994 | Roth | 364/413.25 |
| 5,337,752 A | 8/1994 | Reeves | 128/700 |
| 5,363,401 A | 11/1994 | Lucas et al. | 375/1 |
| 5,365,937 A | 11/1994 | Reeves et al. | 128/175 |
| 5,381,804 A | 1/1995 | Shambroom | 128/731 |
| 5,394,876 A | 3/1995 | Ma | 128/661.09 |
| 5,455,385 A | 10/1995 | Newton et al. | 174/52.4 |
| 5,501,229 A | 3/1996 | Selker et al. | 128/696 |
| 5,551,437 A | 9/1996 | Loetscher | 128/672 |
| 5,553,113 A | 9/1996 | Weedon | 378/98.5 |
| 5,595,188 A | 1/1997 | Kassal | 128/773 |
| 5,598,845 A | 2/1997 | Chandraratna et al. | 128/662.03 |
| 5,617,869 A | 4/1997 | Austin et al. | 128/691 |
| 5,638,823 A | 6/1997 | Akay et al. | 128/691 |
| 5,673,702 A | 10/1997 | Albrecht et al. | 128/712 |
| 5,680,513 A | 10/1997 | Hyland et al. | 395/21 |
| 5,686,917 A | 11/1997 | Odom et al. | 341/141 |
| 5,687,738 A | 11/1997 | Shapiro et al. | 128/715 |
| 5,704,365 A | 1/1998 | Albrecht et al. | 128/702 |
| 5,718,233 A | 2/1998 | Selker et al. | 128/696 |
| 5,724,967 A | 3/1998 | Venkatachalam | 128/633 |
| 5,724,968 A | 3/1998 | Iliff | 128/630 |
| 5,724,983 A | 3/1998 | Selker et al. | 128/696 |
| 5,727,561 A | 3/1998 | Owsley | 128/691 |
| 5,785,657 A | 7/1998 | Breyer et al. | 600/454 |
| 5,796,920 A | 8/1998 | Hyland | 395/22 |
| 5,807,268 A | 9/1998 | Reeves et al. | 600/528 |
| 5,853,005 A | 12/1998 | Scanlon | 128/662.03 |

OTHER PUBLICATIONS

Akay et al., "Application of Adaptive Filters to Noninvasive Acoustical Detection of Coronary Occlusions Before and After Angioplasty," IEEE Transactions on Biomedical Engineering, vol. 39, No. 2, pp. 176–183 (Feb. 1992).

Akay et al., "Noninvasive acoustical detection of coronary artery disease using the adaptive line enhancer method," Medical & Biological Engineering & Computing, vol. 30, pp. 147–154 (Mar. 1992).

Akay et al., "Noninvasive Acoustical Detection of Coronary Artery Disease: A Comparataive Study of Signal Processing Methods," IEEE Transactions on Biomedical Engineering, vol. 40, No. 6, pp. 571–5784 (Jun. 1993).

Donnerstein, "Continuous Spectral Analysis of Heart Murmurs for Evaluating Stenotic Cardiac Lesions," The Am. Journ. Card., vol. 64, pp. 625–630 (Sep. 15, 1989).

Durand et al., "Evaluation of FFT–Based and Modern Parametric Methods for the Spectral Analysis of Bioprosthetic Valve Sounds," IEEE Trans. on Biomedical Eng., vol. BME–33, No. 6, pp. 572–578 (Jun. 1986).

Durand et al: "Spectral analysis and acoustic transmission of mitral and aortic valve closure sounds in dogs" *Medical & Biological Engineering & Computing* 28:4 269–277 (1990).

Foale et al., "Detection of aortic porcine valve dysfunction by maximum entropy spectral analysis," Circulation, vol. 68, No. 1, pp. 42–49 (Jul. 1983).

Fraden, "Application of Piezo/Pyroelectric Films in Medical Transducers," Jour. of Clinical Eng., vol. 13, No. 3, pp. 133–138 (Mar.–Apr. 1988).

Haralick, R. et al., Computer and Robot Vision, Addison–Wesley Publ. Co., NY, NY, pp. 31–40.

Iwata et al., "Algorithm for Detecting the First and Second Heart Sounds by Spectral Tracking," Medical & Biological Engineering and Computing, pp. 19–26 (Jan. 1980).

Johnson et al., "Estimation of the Severity of Aortic Valve Stenosis by Frequency Analysis of the Murmur," J. Am. Coll. Cardiol., 1(5):1315–23 (1983).

Johnson et al., "Evaluation of Aortic Stenosis by Spectral Analysis of the Murmur," JACC, vol. 6, No. 1, pp. 55–65 (Jul. 1985).

Joo et al."Pole–Zero Modeling and Classification of Phonocardiograms," IEEE Trans. on Biomedical Eng., vol. BME–30, No. 2, pp. 110–118 (Feb. 1983).

Kagawa et al., "Real–time sound spectroanalysis for diagnosis of malfunctioning prosthetic valves" J. Thorac. Cardiovasc. Surg., vol. 79, pp. 671–679 (May 1980).

Lees et al., "Phonoangiography: A New Noninvasive Diagnostic Method for Studying Arterial Disease," Proceedings of the National Academy of Sciences, vol. 67, No. 2, pp. 935–942 (Oct. 1970).

Nilsson et al., "A Combined Microphone for Simultaneous Recording of Pulse, Phono and Reference ECG" Electromedica, vol. 2, No. 76, pp. 64–68 (1976).

Oestreicher, "Field and Impedance of an Oscillating Sphere in a Viscoelastic Medium with an Application to Biophysics," J. Acoust. Soc. Am, vol. 23, No. 6, pp. 707–714 (Nov. 1951).

Qian et al., "Orthogonal–Like Discrete Gabor Expansion," 26th Conf. on Infor. Sci an Systems, Princeton University (Mar. 18, 1992).

Semmlow et al., "Coronary Artery Disease—Correlates Between Diastolic Auditory Characteristics and Coronary Artery Stenoses," *IEEE Transactions on Biomedical Engineering*, vol. BME–30, No. 2, pp. 136–139 (Feb. 1983).

Semmlow et al., Noninvasive Detection of Coronary Artery Disease Using Parametric Spectral Analysis Methods, *IEEE Engineering in Medicine and Biology Magazine*, pp. 33–36 (Mar. 1990).

Semmlow et al., "Non–Invasive Diagnosis of Coronary Artery Disease by Enhanced Coronary Phonocardiography," IEEE Frontiers of Eng. in Health Care, pp. 181–185 (1982).

Stein et al., "Frequency Spectra of the First Heart Sound and of the Aortic Component of the Second Heart Sound in Patients with Degenerated Porcine Bioprosthetic Valves," The Am. Journ. of Carad., vol. 53, pp. 557–581 (Feb. 1, 1984).

Verburg, "Transmission of Vibrations of the Heart to the Chestwall," Adv. Cardiovasc. Phys., vol. 5 (Part III), pp. 84–103 (1983).

von Gierke, H. et al., "Physics of Vibrations in Living Tissues," J. App. Physiology, vol. 4, pp. 886–900 (Jun. 1952).

Wang et al., Modeling Sound Generation in Stenosed Coronary Arteries, IEEE Transactions on Biomedical Engineering, vol. 37, No. 11, pp. 1087–1094 (Nov. 1990).

ACOUSTIC SENSOR ARRAY FOR NON-INVASIVE DETECTION OF CORONARY ARTERY DISEASE

RELATED APPLICATIONS

This application is a second divisional of U.S. application Ser. No. 09/188,434 filed Nov. 9, 1998, now U.S. Pat. No. 6,193,668, and claims priority from the first divisional thereof, U.S. application Ser. No., 09/734,448, filed Dec. 11, 2000, to be issued as U.S. Pat. No. 6,478,746, the contents of each are hereby incorporated by reference as if recited in full herein. This application is related to co-assigned U.S. Patent application entitled "Non-Invasive Turbulent Blood Flow Imaging System" identified by Attorney Docket No. 9023-11 which corresponds to PCT/US97/20186 filed Nov. 10, 1997 ("the 20186 application"), now U.S. Pat. No. 6,278,890. This application is also related to co-assigned patent application Ser. No. 09/136,933, entitled "Thin Film Piezoelectric Polymer Sensor" now U.S. Pat. No. 6,261,237 and co-assigned Patent Application identified by Attorney Docket No. 9023-16 entitled "Acoustic Window Identification", now U.S. Pat. No. 6,371,924. The contents of the above-identified applications/patents are hereby incorporated by reference as if recited in full herein.

FIELD OF THE INVENTION

This invention relates to arrays of acoustic sensors that facilitate the non-invasive detection of coronary artery disease (CAD).

BACKGROUND OF THE INVENTION

The 20186 application describes an invention for the non-invasive in vivo detection and localization of abnormal blood flow. Embodiments of that invention display the spatial distribution of phase coherence in the shear eave component of blood flow signals generated by an acoustic sensor array. An essentially uniform display indicates normal blood flow. A non-uniform display may indicate the presence of an occlusion and the presence or extent of abnormal, turbulent blood flow. Poor correlation of signals from the array sensors may adversely affect the display uniformity.

Acoustic sensor arrays are conventionally positioned above a measurement area defined as the hairless human chest skin located vertically between the sternum and a parallel line passing through the left nipple and horizontally 10 cm above and 6 cm below the left and right nipples.

A prior art acoustic sensor array comprising eight equally spaced sensors in two concentric circles having prime numbers of sensors in each circle and a ninth sensor at the common center of the concentric circle is illustrated by FIG. 6 of the 20186 application.

To reach sensors in a conventionally positioned prior art array as described in the 20186 application, sound waves must travel either directly through lung tissue or first to the body surface and then laterally with consequent attenuation of correlation. A study of the correlation by that array of patient data signals generated by the quiet interval revealed that only four or five of the nine sensors are well correlated.

It is known that a notch ("cardiac notch") in the human left lung allows the heart to be in contact with the chest wall. Well correlated blood flow signals may be generated by acoustic sensors positioned on a human chest in a small area ("acoustic window") located above the cardiac notch. The bounds of the acoustic window have been approximated by ultrasonic probe means as described in this application and by locating the portions of sensor corresponding to channels achieve the highest apparent signal to noise ratio (SNR) as described in the Stearns application.

Definitions

Acoustic Window—An area above the notch in the human left lung which allows the heart to be in contact with the chest wall. Well correlated acoustic blood flow signals of good quality may be generated by a sensor array positioned on a patient's chest within or substantially within the perimeter of an acoustic window.

Sensor or Accelerometer—Any current or voltage mode device which generates an electric signal from displacement or a derivative thereof upon detection of a sound wave.

Sensor Array—A pattern or spaced arrangement of a plurality of sensors on or to be placed on the body surface of a patient.

Sensor Array Aperture—The space or area within the perimeter of an array.

Sensor Array Geometry—The shape of the perimeter of a sensor array.

Channel—The path to a receiver followed by a signal from the sensor by which the signal is generated.

SUMMARY OF THE INVENTION

Pursuant to one embodiment of the invention, an acoustic window may be defined by ultrasonic probe means. The invention includes sensor arrays having an aperture locatable within or substantially within the bounds of an acoustic window when the array is positioned on the chest of a person.

An important aspect of the invention includes the identification of an acoustic window comprising the merged acoustic window sub-areas corresponding to two or more intercostal spaces (ICS's), and array designs to accommodate such acoustic windows.

DETAILED DESCRIPTION OF THE INVENTION

The invention generally comprises the identification of an acoustic window and the design of arrays having geometry sized to fit within or substantially within and thus accommodate the perimeter of the window. The invention may include an average acoustic window and consolidated or merged window subareas and array geometry sized accordingly.

Ultrasonic Probe Determination of the Size and Location of the Acoustic Window-Design of Template for Sensor Positioning The acoustic window may include one or a combination of the small areas (intercostal space window areas) of the patient's chest surface directly above the intercostal spaces one through six. Determination of the size of an acoustic window may be accomplished by steps (i) to (v).

(i) With the patient supine, i.e., lying on his back or side, draw a series of dots along the left sternal border at the beginning of each intercostal space (ICS) for spaces one through six.

(ii) Place an ultrasound probe at the left sternal border of the first intercostal space (ICS). Then move the probe along the intercostal space until the lung tissue is encountered. Place a dot on the chest to mark where the lung tissue begins.

(iii) Repeat step (ii) for intercostal spaces two through six.

Figure 1:
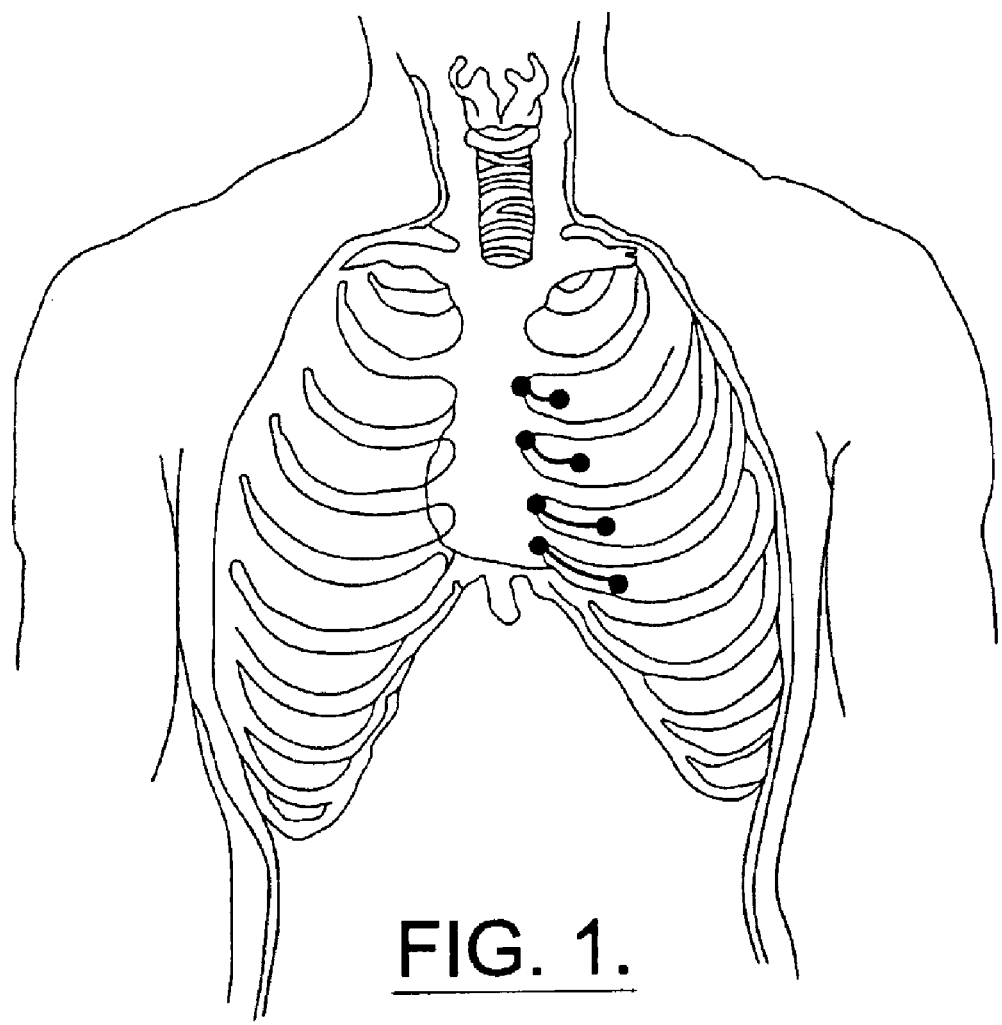
FIG. 1 illustrates an ultrasonic probe acoustic window characterization method that provides a template for the positioning of sensors on a person's chest. All acoustic window data illustrated by FIGS. 2 through 8 and 10 through 12 was obtained by the FIG. 1 method.

(iv) Wipe the ultrasound gel off the chest, and draw a line following each intercostal space, connecting the two previously drawn dots. The lines should be similar to FIG. 1.

(v) After the chest has been marked as above, place a sheet of tracing paper on the chest, and transfer the markings onto the paper to provide a template for positioning of sensors.

Average or "generic" templates may be prepared from average data determined in the same way from a plurality of persons.

A like procedure may be used to determine an acoustic window of a person lying slanted on a bed.

Table 1 lists the window areas in cm-squared for the three window sizes in two bed positions. For the maximum and average window cases, lying slanted on the bed produces a slightly larger (5% and 16%, respectively) window size than lying flat on the bed. In the case of the minimum window, lying flat does produce a significant 37% larger window area than lying slanted on the bed.

TABLE 1

Differences in the Flat and Slanted Bed Positions

| Areas in cm | Average Area | Maximum Area | Minimum Area |
|---|---|---|---|
| Slant Position | 58.08 | 134.46 | 6.73 |
| Flat Position | 48.82 | 127.37 | 9.22 |
| % Difference | 15.94 | 5.26 | −36.87 |

Based on these results, the flat position is more advantageous since it does not significantly reduce the acoustics window for subjects with large to medium window sizes and at the same time significantly opens up the smaller acoustic window sizes.

Another method for identifying an acoustic window entails examination of which sensor channels receive the highest signal to noise ratio (SNR) as measured by the optimal weights for summing channels. See copending, commonly assigned Stearns U.S. application.

Statistical Analysis of Acoustic Window Data

Acoustic window size data, collected pursuant to the described ultrasonic probe methodology, was obtained from 22 male and 7 female subjects. There are two types of data.

1. Measurements based on a Cartesian coordinate with X axis on the $6^{th}$ intercostal space (ICS) and Y axis along the left end of the ICS.

2. Data estimate in polar coordinate centered at the centroid of the acoustic window mass. This data is derived from measuring the distance from the centroid to the edge of the window at 30 degree angle increments. There is a total of twelve data points per subject.

The Distribution of Polar Data

Figure 2:
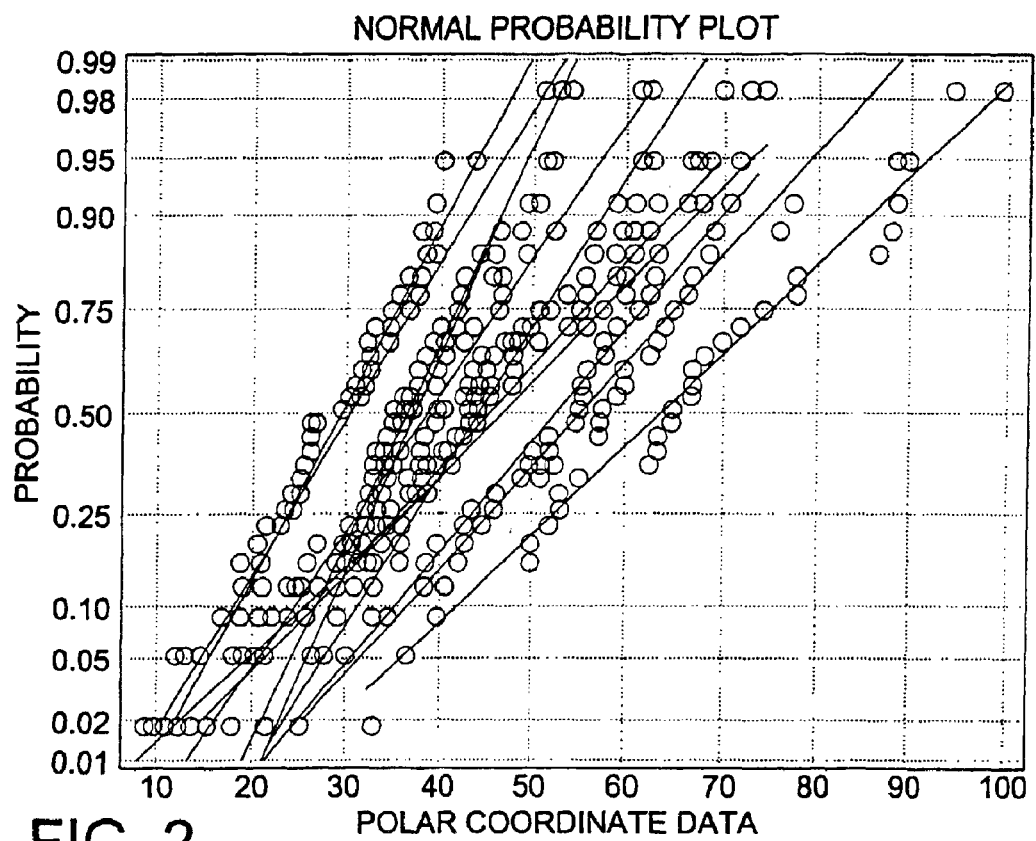
FIG. 2 is a plot in polar format of the acoustic window size data obtained from 22 male and 7 female subjects (29 subjects).

The distribution of the window size data in polar format was tested for normality using the normal probability plot from the MATLAB Statistics Toolbox. The purpose of a normal probability plot is to graphically assess whether the data could come from a normal distribution. If the data are normal, the plot will be linear. Other distribution types will introduce curvature in the plot. As shown in FIG. 2, the data points are virtually in a straight line, indicating that the polar coordinate data is Gaussian.

Figure 3:
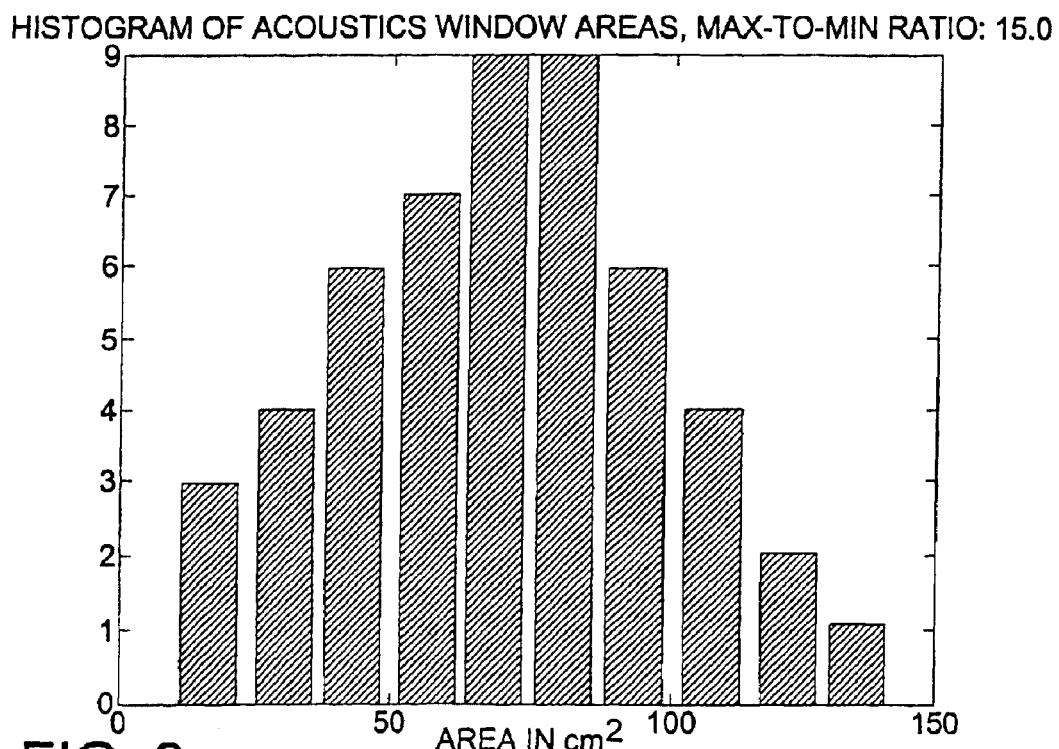
FIG. 3 is a histogram of the window areas of the same 29 subjects from which the FIG. 2 data was obtained.

When the area for each of the 22 male windows was computed using AutoCad software, the ratio of the maximum to the minimum area was found to be 15. FIG. 3 illustrates the histogram of the window areas.

Figure 4:
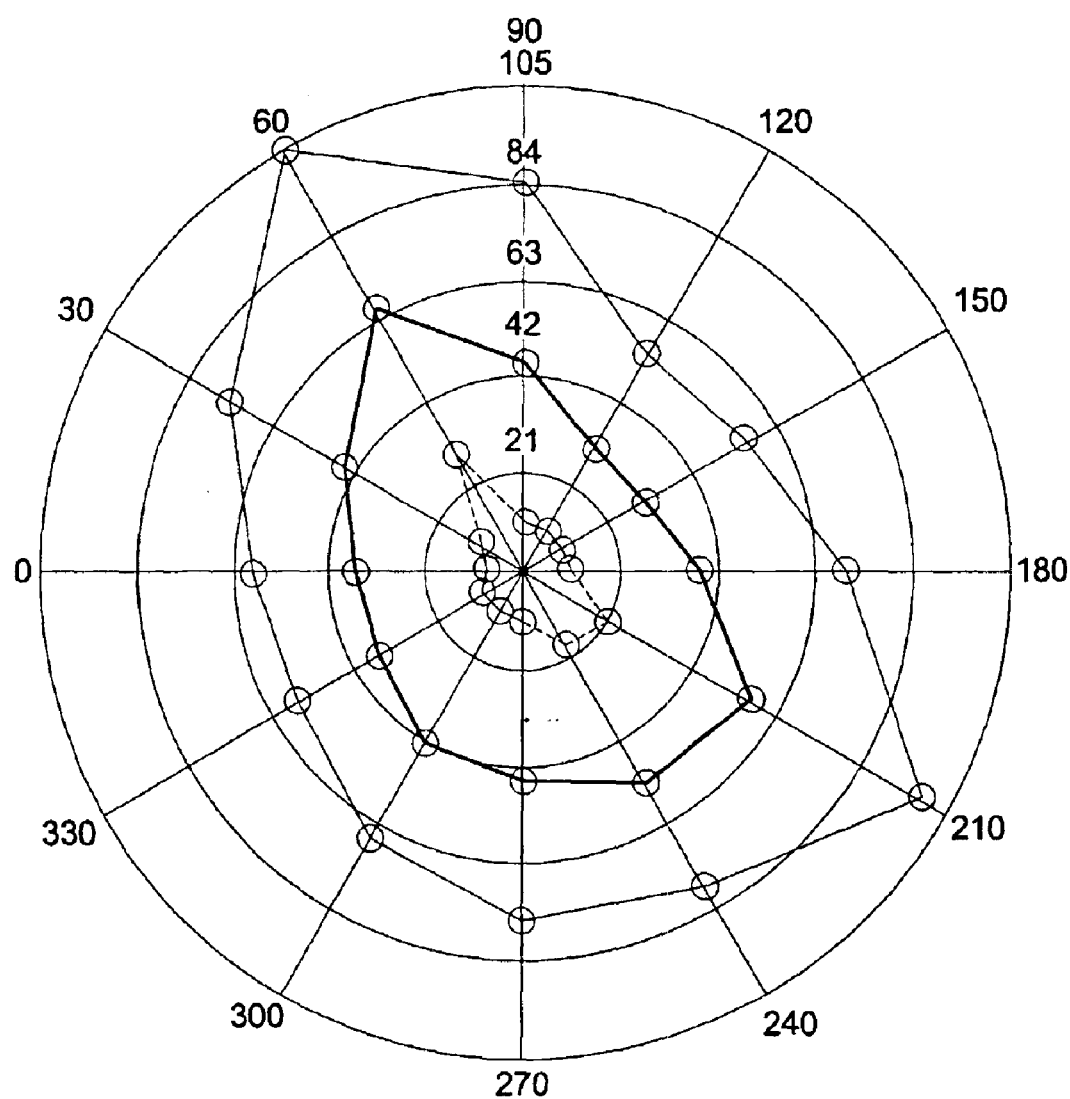
FIG. 4 shows acoustic window size in polar format. Maximum, minimum and average window size for-all of the same 29 subjects is depicted.

FIG. 4 shows the acoustics window size in polar format. In this figure, the outside perimeter is for maximum, the inside perimeter is for the minimum and the intermediate perimeter is for the average across all subjects.

Correlation Coefficients Between Acoustics Window Areas and Demographic Data Computed correlation coefficients between the window area and the subject demographics data are shown in Table 2. This analysis was carried out based on data broken down by male (22 subjects), female (7 subjects) and a combination of both sexes. In general, there exists no strong correlation between the window area and demographics data, with the exception of strong negative correlation of −0.84 between the acoustics window area and the anterior/posterior (AP) diameter of the female subjects and a strong negative correlation between the acoustics window area and the sternum length in both male and female subjects.

Variations of the ICS End Points in Cartesian Coordinate

Examination of the data in Cartesian coordinate reveals the absence of common single reference point such as the centroid in the polar data case. The X-Y data was collected relative to the six intercostal spaces and was measured as left and right ICS. The only single common reference was made when the six ICS's were aligned on the x-axis so that the other spaces can be seen relative to this reference space.

Figure 5:
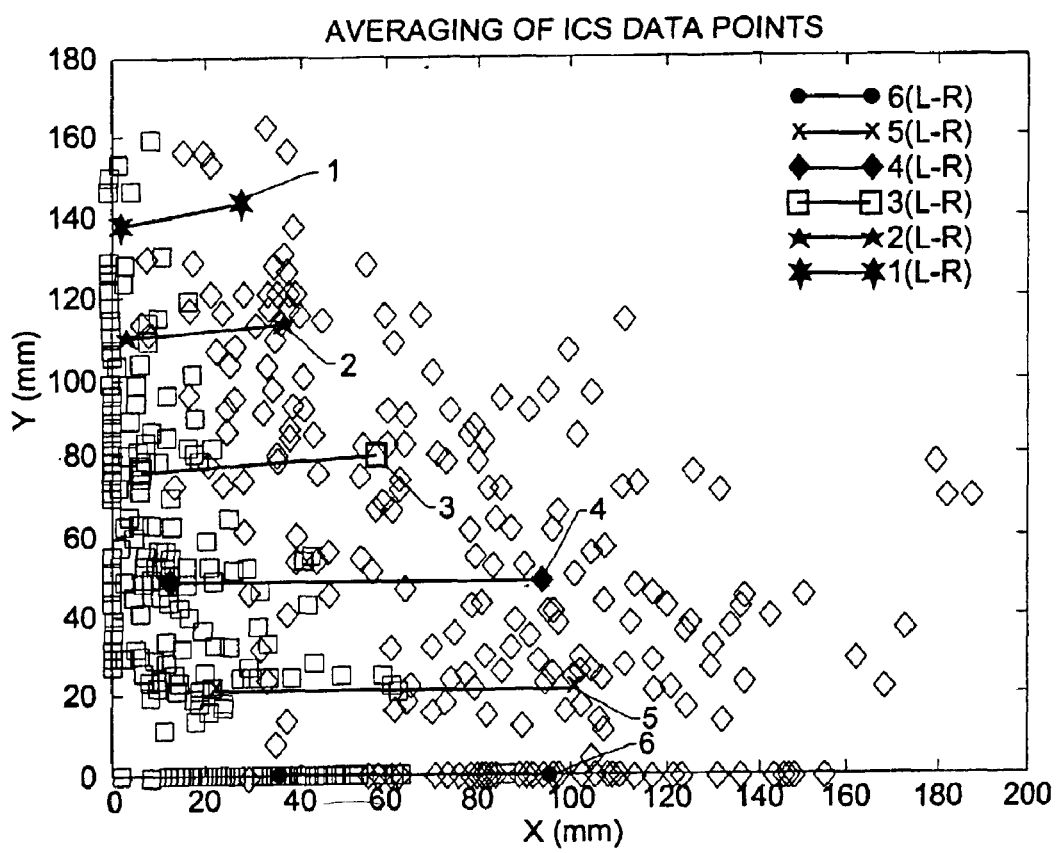
FIG. 5 illustrates in Cartesian coordinates variations of the ICS ultrasonic probe data points from the left (□) and right (◇) ICS. The statistical averages for ICS's 1 to 5 are shown in solid lines. A perimeter connecting the ends of the solid lines is a visualization of the average geometry of the six intercostal spaces.

As seen from FIG. 5, the XY coordinates of the left in (□) and right in (◊) ICS are quite different across the subjects. The statistical averages of the left and right ICS are also shown. When connected, a visualization of the average geometry of the six intercostal spaces is provided.

The Distribution of Window Centroids Over ICS

The x-y coordinates of the acoustics window centroids were measured and correlated with the lines defined by the left and right ICS. The purpose of this correlation is to determine which of the six spaces the window centroid is near to and then to ascertain the best space(s) for location of the array.

Figure 6:
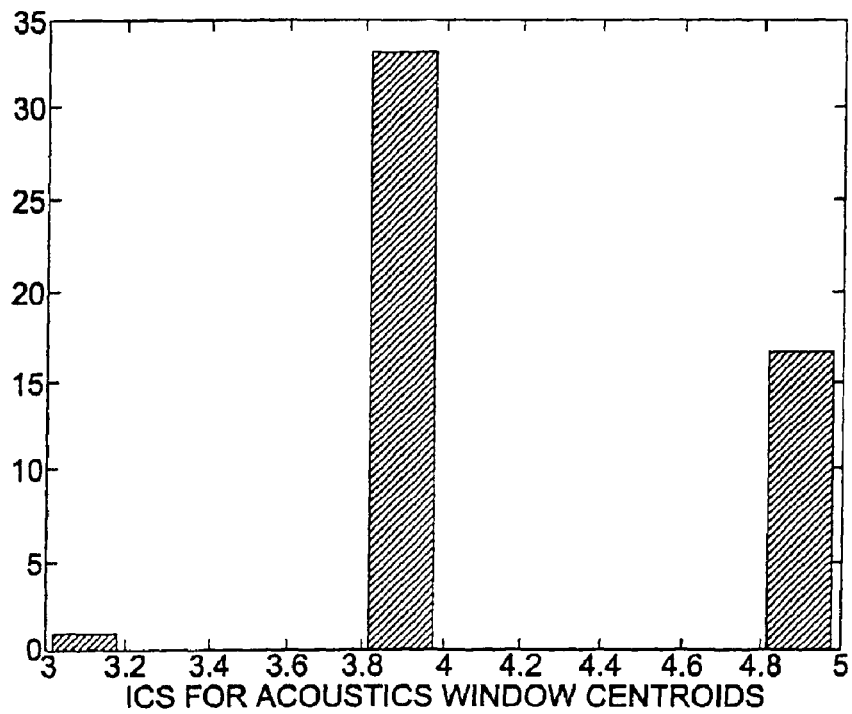
FIG. 6 is a histogram that indicates ICS nearest to the centroids of the average window area (see FIG. 4).

A histogram of the ICS to which the centroids of the window areas are nearest is plotted in FIG. 6. The result indicates that the fourth and fifth ICS are good candidates for positioning the array center, with the fourth ICS being more frequent than the fifth ICS. In practice, it is appropriate to consider these two ICS equally and pick one based on the best knowledge of which ICS has the best heartbeat sound.

Figure 7:
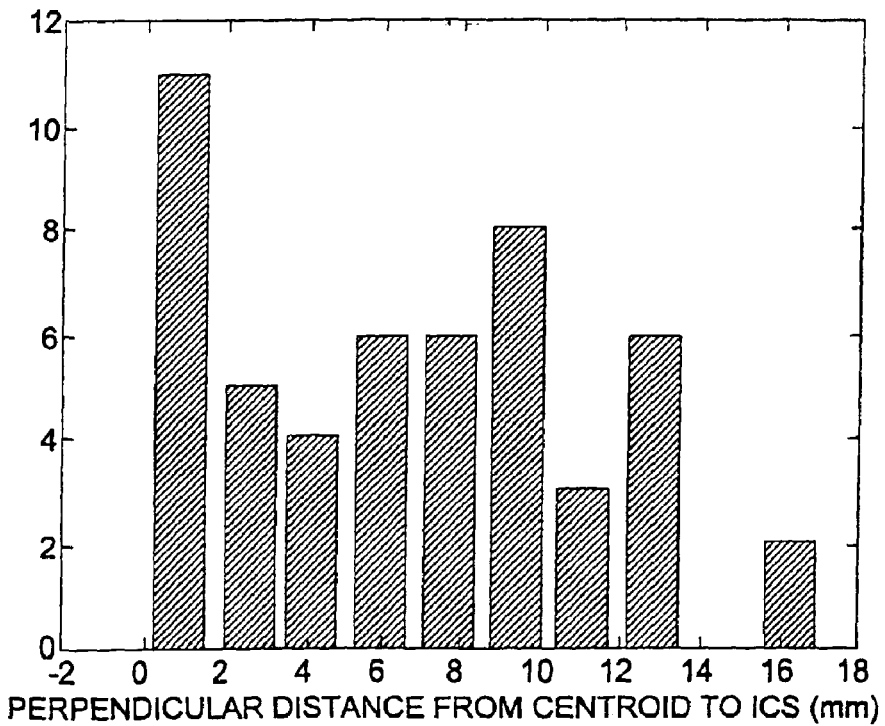
FIG. 7 is a histogram indicating the distribution of the perpendicular distances from the centroid of the average window area (see FIG. 4) to the nearest ICS.
Figure 8:
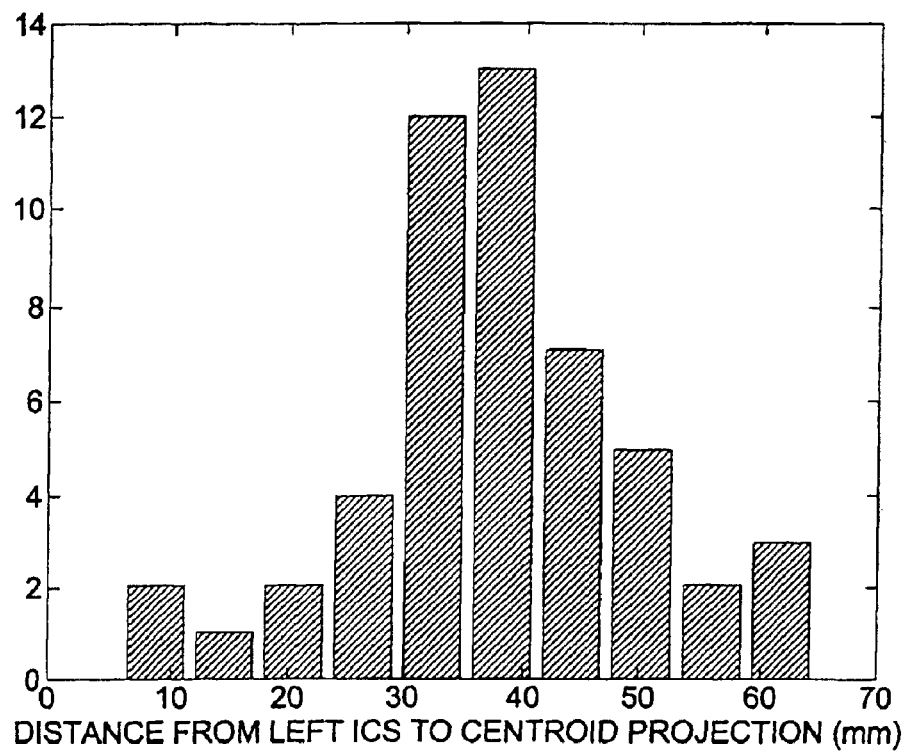
FIG. 8 is a histogram illustrating the distribution of the distance from the left side of the nearest ICS to the projection of the centroid of the average window area (see FIG. 4).
Figure 9:
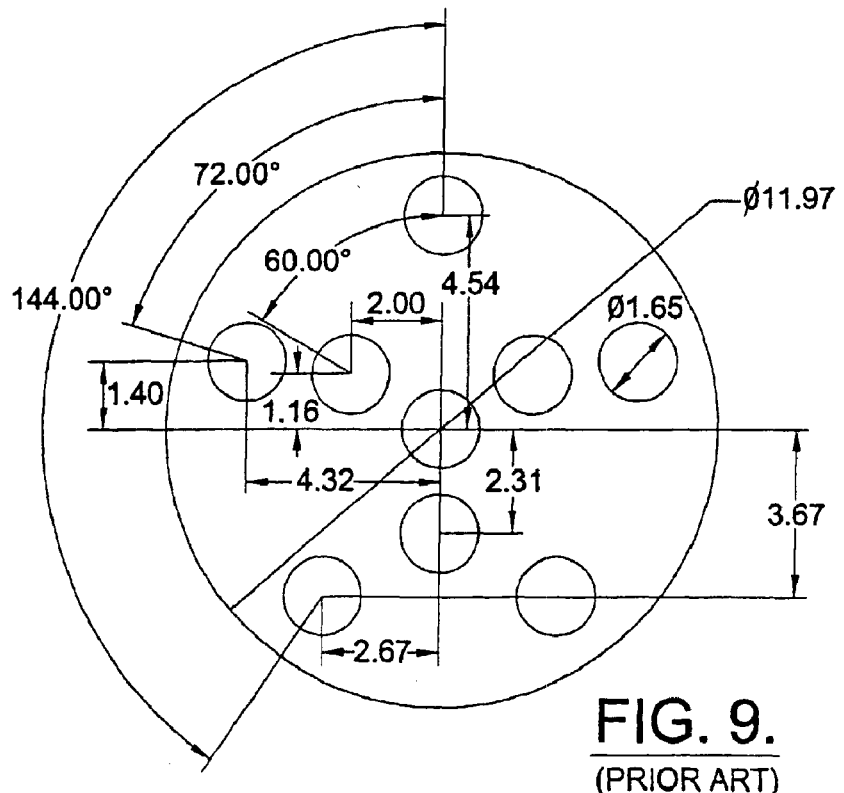
FIG. 9 depicts a prior art nine sensor array based on seismic accelerometers commercially available from Wilcoxon Research, 21 Firstfield Road, Gaithersburg, Md. 20878. The array comprises eight equally spaced sensors in two concentric circles having prime numbers of sensors in each circle and a ninth sensor in the common center of the concentric circles.

The distribution of (a) the perpendicular distances from the centroid to the nearest ICS and (b) the distances from the left side of the nearest ICS to the projection of the centroid are histogrammed in FIGS. 7 and 8. These results provide guidelines as to the approximate location of the array center relative to the nearest intercostal space.

Array Design Based on Acoustics Window Data Factors and Constraints in Array Geometry Design Constraints imposed on array geometry include:

1. Limitation on the array aperture by the size of the acoustics window which varies from person to person.

2. Sensor size which limits the number of elements that can be put in the array aperture. For example, the medical Wilcoxon sensor diameter is about one cm. In the case of PVDF sensor, the prefabricated thin film strip size dictates how many sensors could be placed in the array aperture.

3. The anti-aliasing requirement of the array design at different operating frequencies. In principle, the inter-element spacing of the sensors is required to be less than half a wavelength at the highest operating frequency to avoid spatial aliasing in the plane wave case. This requirement is relaxed in the near field where source location is the objective. The use of irregularity in array geometry may also alleviate the aliasing problem when there is an inter-element spacing of more than half wavelength.

Array Geometries

Figure 10:
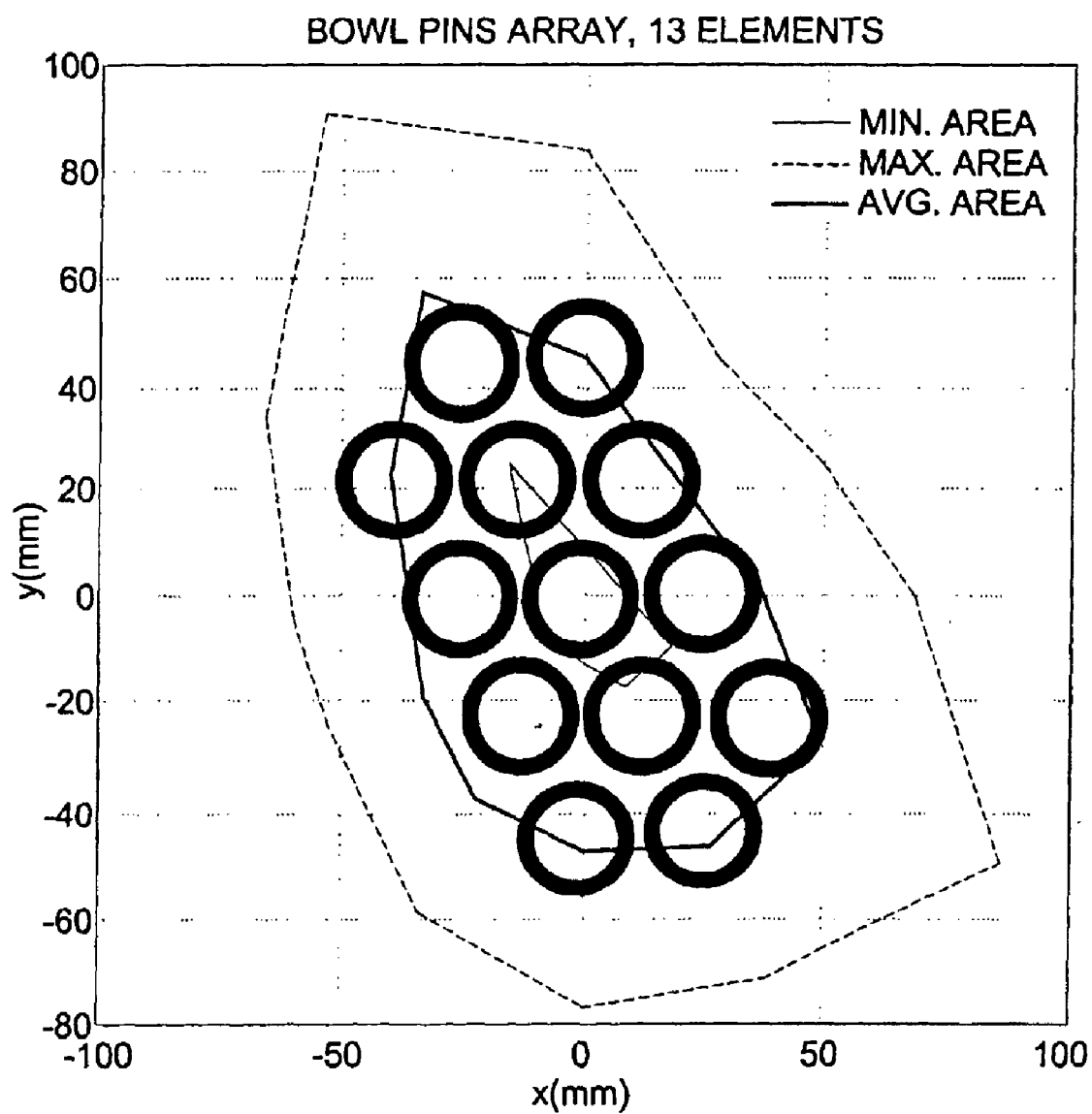
FIG. 10 depicts a 13 element array positioned over an acoustic window of average size (solid line, see FIG. 4). An acoustic window of maximum area is also shown (broken line).
Figure 11:
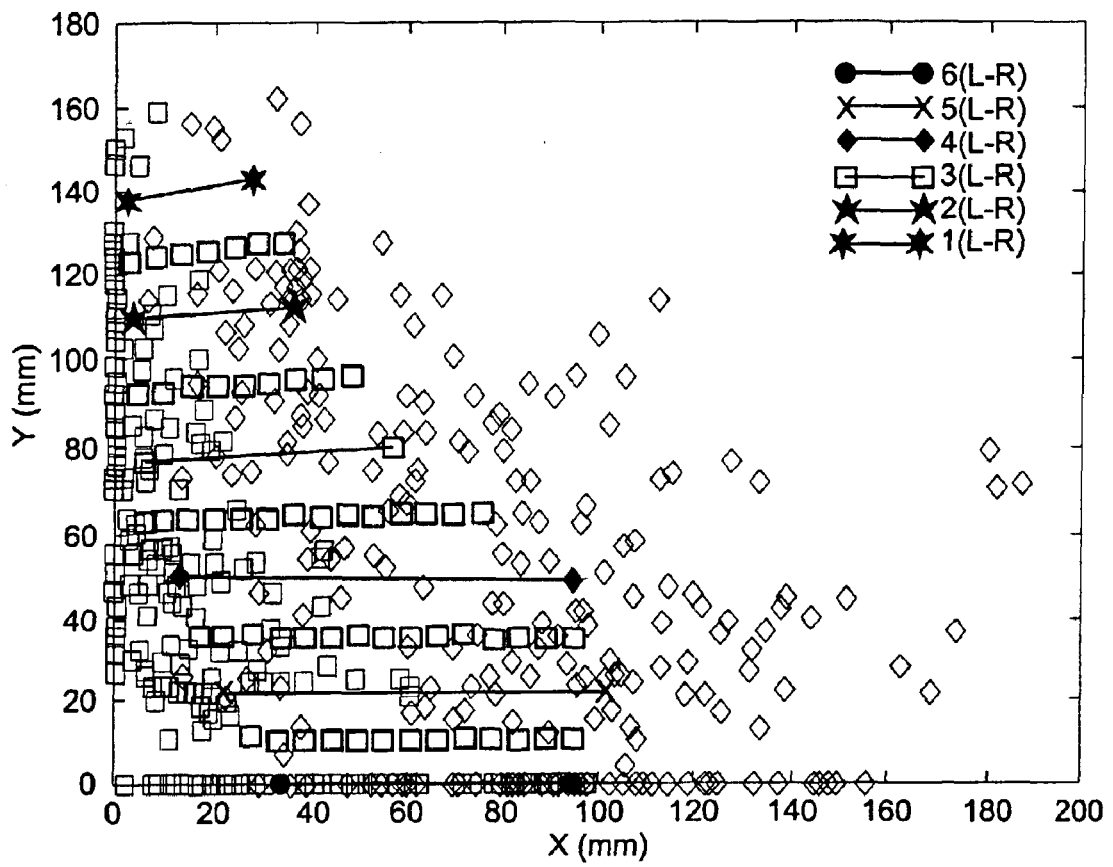
FIG. 11 illustrates a 57 element small PVDF sensor array based on averaging of ICS data points. The array comprises five linear subarrays positioned above intercostal spaces 2 to 6.
Figure 12:
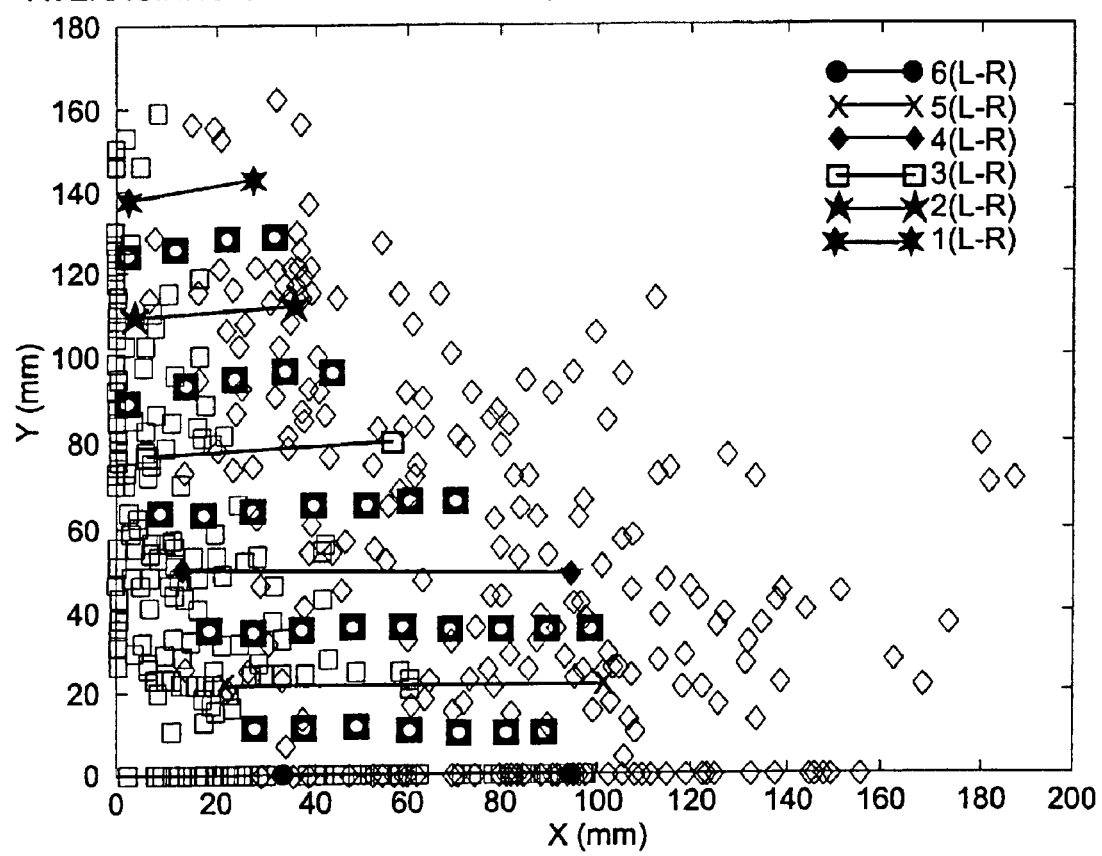
FIG. 12 illustrates a 32 element array of large PVDF sensors based on averaging of ICS data points. The array comprises five linear subarrays positioned above intercostal spaces 2 to 6.

Use of the acoustics window in array design based on the medical Wilcoxon accelerometer and the large and small PVDF sensors resulted in the three arrays depicted by FIGS. 10, 11 and 12.

The 13-element array of FIG. 10 was based on the average window size described with reference to FIG. 4. Using the actual dimensions of the medical Wilcoxon accelerometer on graph paper, each accelerometer was placed on straight lines starting from the center and populating the perimeter until space is occupied. A total of 13 elements that were fitted into this average window size. Clinical data indicates that 13 elements may not give optimum array gain especially when element signal-to-noise ratio of turbulent flow is low.

More elements per unit area are possible with PVDF technology. Because PVDF film is available in linear strips of 9 and 16 elements per unit, each strip can be put on the intercostal space to maximize signal reception. These factors motivate the array geometries illustrated in FIGS. 11 and 12.

TABLE 2

| Demographic Feature | Correlation w/ Acoustics Window Area (M&F) | Correlation w/ Acoustics Window Area (Male) | Correlation w/ Acoustics Window Area (Female) |
|---|---|---|---|
| Age | 0.0043 | 0.0152 | −0.0095 |
| Height | −0.1846 | −0.4345 | 0.2794 |
| Weight | −0.3503 | −0.3579 | −0.6678 |
| Chest Circumference | −0.3578 | −0.3800 | −0.3623 |
| AP Diameter | −0.5904 | −0.5027 | −0.8690 |
| Aortic Valve Depth | 0.1868 | −0.0043 | 0.5311 |
| ICS of Aortic Valve | −0.0774 | −0.2801 | 0.1810 |
| Sternum Length | −0.6446 | −0.6959 | −0.6587 |
| Body Type | −0.0874 | −0.1637 | 0.0604 |

In these two arrangements, five lines of PVDF film strip are placed along ICSs 2 to 6 at approximately the length of the average ICS as described with reference to FIG. 5. The placement of these PVDF film strips as shown in FIGS. 11 and 12 are for illustration only and not necessarily the exact position and direction of the film strips. Also, because of the inherent variations in human anatomy, the actual placement of the PVDF sensor strips is expected to be different from person to person, in view of the effect of the ribs as a factor in signal reception.

At the end, 57 elements for the small PVDF and 32 elements for the large PVDF sensors were used in this array design.

Array Performance

Figure 13:
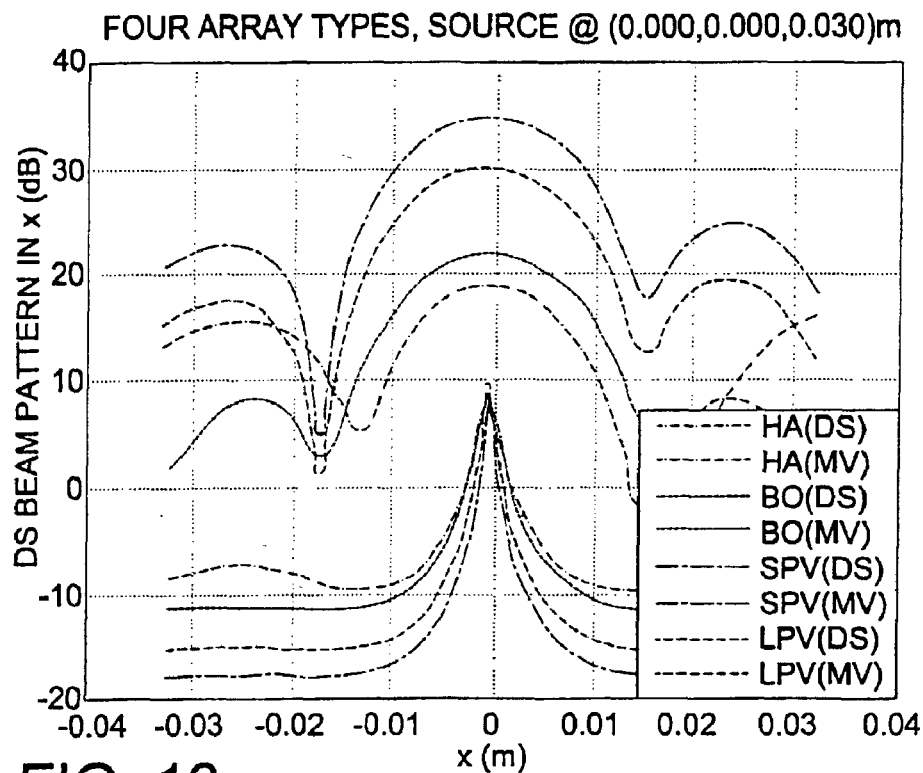
FIG. 13 illustrates a beam pattern in x for delay-and-sum (DS) (higher in value) and MVDR (lower in value) beamformers using prior art (HA) (dashed lines), bowling pin (BO) (dashed dotted lines), small PDVF (SP) (solid lines) and large PDVF (LP) (dotted lines) arrays.
Figure 14:
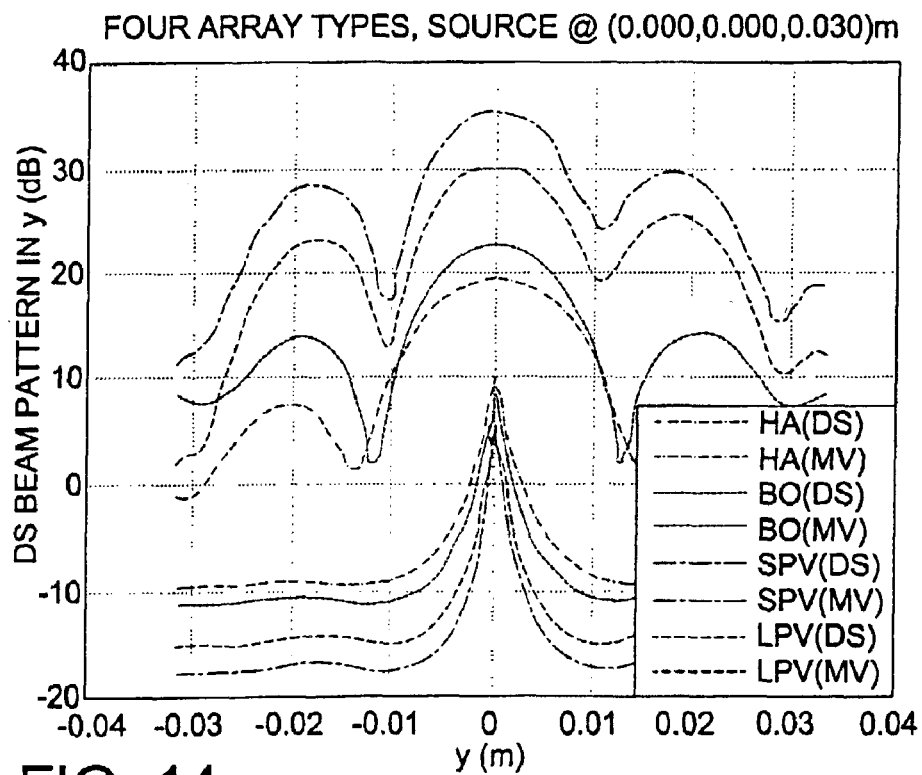
FIG. 14 illustrates a beam pattern in y (dB) for delay-and-sum (DS) (broken lines) and MVDR (solid lines) beamformers using prior art (HA), bowling pin (BO), small PDVF (SP) and large PDVF (LP) arrays.
Figure 15:
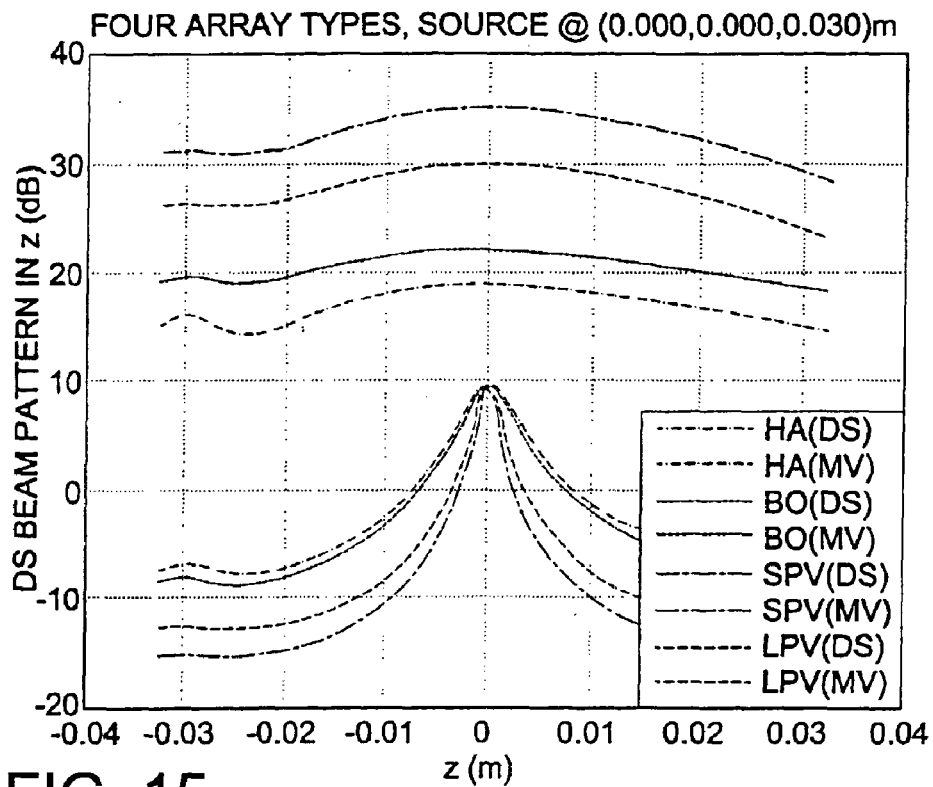
FIG. 15 illustrates a beam pattern in z (dB) for delay-and-sum (DS) (broken lines) and MVDR (solid lines) beamformers using Harris (HA), bowling pin (BO), small PDVF (SP) and large PDVF (LP) arrays.

The performance of the four sensor arrays depicted by FIGS. 9, 10, 11 and 12 is presented in terms of beam width and array gain by FIGS. 13, 14 and 15. The beam pattern plots are for frequency at 250 Hz using Verberg propagation model and 10 dB element SNR. These figures show the beam patterns in x, y and z direction for a source 3 cm directly below the array center. The beam pattern for the conventional delay and sum (DS) beamformer is shown in dashed line, and the beam pattern for the MVDR beamformer is in solid line.

The figures show that for a conventional beamformer, the array gain is proportional to the number of elements. The effect of the number of elements on the array beamwidth is much more visible for the MVDR beamformer than for the DS beamformer. Also notable is the lack of array aperture in the z direction, as illustrated by the large beam width shown in FIG. 15.

It is known that the MVDR beamformer provides an estimate of the signal power at the signal direction as can clearly be seen from FIGS. 13, 14 and 15. At the source location, the output of the MVDR beamformer is 10 dB regardless of the number of element in the array. The effect of an increase in the number of elements is a narrower beam width, which is consistent with data showing that the beam width of an MVDR beamformer is inversely proportional to the number of elements (and the element SNR).

Array Geometries

Increasing the number of elements in constrained by acoustics window size and the physical dimensions of the individual sensor.

It became apparent from the performance of the array designs of FIGS. 10 to 14 that the use of the $4^{th}$ and $5^{th}$ intercostal spaces for centering purpose has merit in the array design process. For both designs, the acoustics window is the union of the two window areas for the $4^{th}$ and $5^{th}$ ICSs. These two windows are the average of the XY data obtained from the acoustics window study. The merging of the two windows increases the area available for the array aperture which is an advantage to array performance.

A Proposed Wilcoxon Accelerometer Array Based on the Dominant ICS Areas

Figure 16:
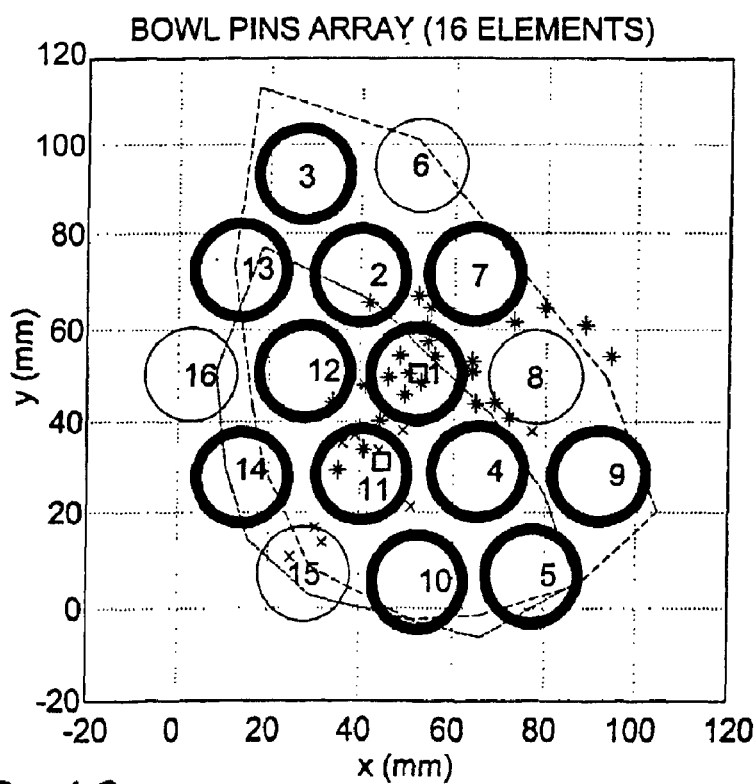
FIG. 16 is a proposed array based on the medical Wilcoxon accelerometer. Only 12 elements are used due to the limitation of the data collection system. The broken line indicates the perimeter of an acoustic window.

A design for a Wilcoxon commercial accelerometer array is shown in FIG. 16. In this design, there are a total of 16 elements that will fit the composite window area. The composite window area consists of the two averaged windows with centroids near the $4^{th}$ and $5^{th}$ ICSs. In the current data collection system, only 12 elements are used. The missing elements are chosen such that the resulting array is as irregular as possible with at least one sensor pair very close to each other to prevent spatial aliasing.

A PVDF Sensor Array

Figure 17:
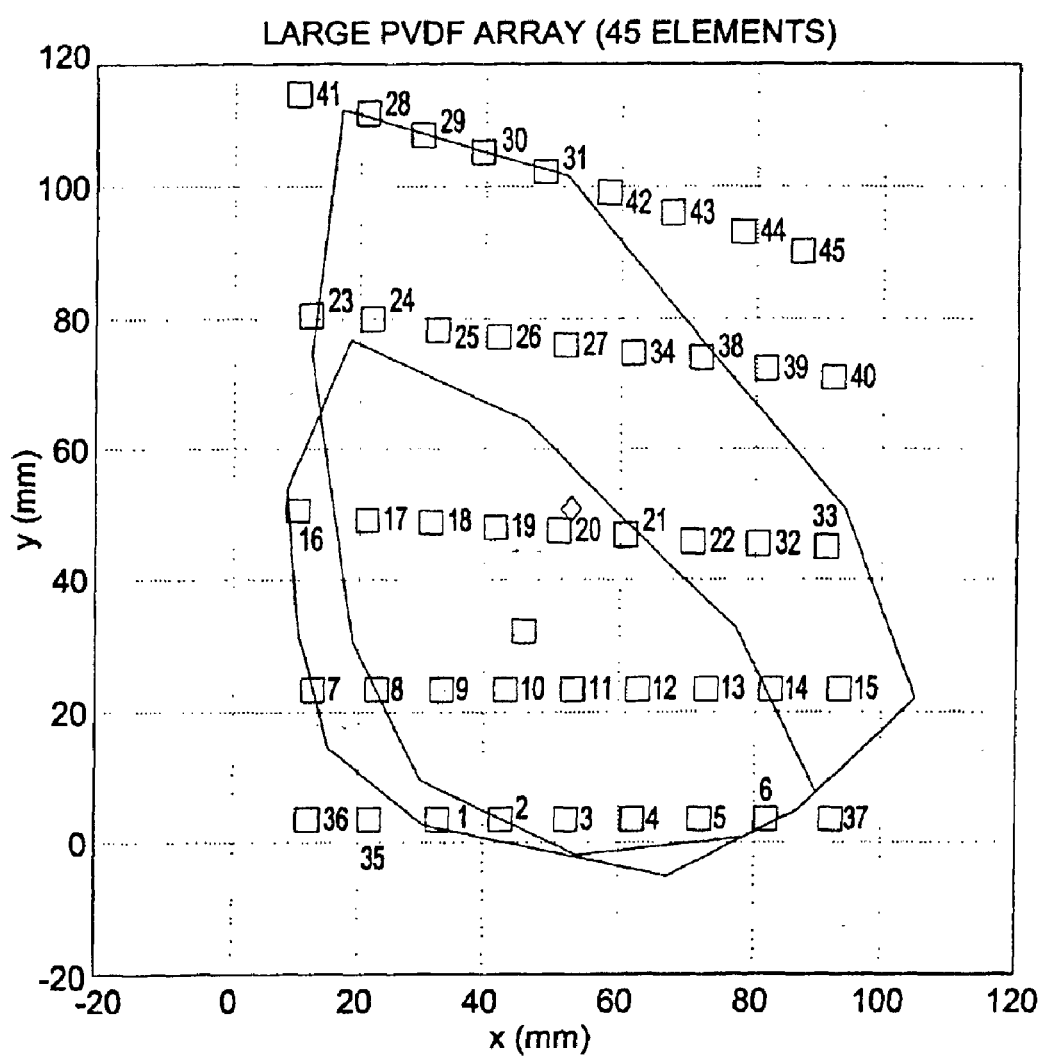
FIG. 17 illustrates a 45-element PVDF-sensor array comprising five nine element linear subarrays positioned above intercostal spaces 2 to 6. Large and small acoustic window perimeters with centroids near the fourth and fifth ICS's are shown.

For the same composite acoustics window, a 45-element PVDF array is shown in FIG. 17. This array essentially consists of 5 rows of 9-element large PVDF linear array arranged in such a way that conforms to the human chest curvature and, if possible, lies within the lower ICS to adapt to the patient anatomy. One reason for a 5 by 9 linear PVDF array is in the manufacturing and logistics of the thin film technology.

It may not be possible to use all 45 elements for beamforming, since some of the array elements may fall out the acoustics window and thus will not be able to receive the heart sound. An acceptable data collection scheme includes estimation of the signal-to-noise ratio at each element, and weighting or eliminating the sensors that receive the noisiest signal. The use of this weighting technique enables the array to adapt to the differences in acoustic window size that are embodied in human anatomy.

What is claimed is:

1. A method for visualizing the acoustic window of a person, which comprises:

(i) causing a person to assume a supine position;

(ii) drawing a series of indicia on the chest of the person along the left sternal border at the beginning of each intercostal space for each of a selected plurality of intercostal spaces 1 to 6 of the person;

(iii) placing a probe at the left sternal border of each of the selected intercostal spaces and moving said probe along each of the intercostal spaces until lung tissue is encountered;

(iv) placing an indicator on the chest of the person to identify as to where at each intercostal space lung tissue is encountered; and (v) drawing a series of lines connecting said lung indicator indicia to the left sternal border on the chest of the person, wherein said lines indicate the bounds of the acoustic window perimeter of one corresponding intercostal space.

2. The method of claim 1, further comprising visualizing a boundary line with a perimeter geometry that encloses all of said individual intercostals space lines to define total acoustic window space of the person.

3. The method of claim 2, further comprising determining an acoustic window centroid of the total acoustic window space.

4. The method of claim 1, wherein the plurality of selected intercostals spaces includes at least spaces 4 and 5.

5. The method of claim 4, wherein the plurality of selected intercostals spaces includes all spaces 1–6.

6. The method of claim 1, wherein the probe is an ultrasound probe.

7. The method of claim 1, further comprising providing a sensor array with a plurality of sensor elements and arranging the sensor array on the patient so that the sensor elements occupy a major portion of and extends substantially within the total visualized acoustic window space.

8. The method of claim 7, wherein the sensor array includes about 32 sensor elements.

9. The method of claim 8, further comprising non-invasively determining if the patient has coronary artery disease.

10. The method of claim 7, wherein the sensor elements are configured to non-invasively detect heart and/or blood flow sounds.

11. The method of claim 10, wherein the sensor elements are acoustic sensors.

12. The method of claim 7, further comprising providing a sensor array and arranging the sensor array on the patient so that it's sensor elements extend across a major portion of the lines of the selected intercostals spaces but substantially within the total visualized acoustic window space.

13. The method of claim 7, wherein the sensor array is a polyvinyldifluoride (PVDF) sensor array.

14. The method of claim 7, wherein the sensor elements are piezoelectric film sensors.

15. The method of claim 7, wherein the sensor array is a plurality of spaced-apart linear sensor arrays.

16. The method of claim 15, wherein each of the linear sensor arrays are positioned on the person above selected respective intercostals spaces.

17. The method of claim 7, wherein the sensor array comprises accelerometer sensor elements.

18. The method of claim 7, wherein the sensor array comprises a linear array of about five rows or less each comprising about 9 elements or less.

19. The method of claim 7, wherein the sensor array includes between about 13–57 elements.

20. The method of claim 7, wherein the sensor array includes a plurality of linear subarrays, the method further comprising arranging the subarrays so that sensor elements are positioned above intercostals spaces 2–6.

* * * * *